US009494559B2

(12) United States Patent
Forster

(10) Patent No.: US 9,494,559 B2
(45) Date of Patent: Nov. 15, 2016

(54) SYSTEM AND METHOD FOR RFID-BASED REMOTE MATERIAL ANALYSIS

(71) Applicant: Avery Dennison Corporation, Mentor, OH (US)

(72) Inventor: Ian James Forster, Essex (GB)

(73) Assignee: AVERY DENNISON RETAIL INFORMATION SERVICES, LLC, Westborough, MA (US)

( * ) Notice: Subject to any disclaimer, the term of this patent is extended or adjusted under 35 U.S.C. 154(b) by 226 days.

(21) Appl. No.: 14/054,243

(22) Filed: Oct. 15, 2013

(65) Prior Publication Data

US 2014/0102198 A1    Apr. 17, 2014

Related U.S. Application Data

(60) Provisional application No. 61/714,357, filed on Oct. 16, 2012.

(51) Int. Cl.
| | | |
|---|---|---|
| *G01N 29/12* | (2006.01) | |
| *G01N 29/04* | (2006.01) | |
| *G01N 29/24* | (2006.01) | |
| *G08C 17/02* | (2006.01) | |

(52) U.S. Cl.
CPC .............. *G01N 29/04* (2013.01); *G01N 29/12* (2013.01); *G01N 29/2437* (2013.01); *G01N 29/2481* (2013.01); *G08C 17/02* (2013.01); *G01N 2291/02475* (2013.01)

(58) Field of Classification Search
CPC .. G01N 29/04; G01N 29/2437; G01N 29/12; G01N 29/2481; G01N 2291/02475; G01N 3/40; G01N 3/405
USPC .................................. 73/573, 579, 582, 583
See application file for complete search history.

(56) References Cited

U.S. PATENT DOCUMENTS

| | | | | |
|---|---|---|---|---|
| 3,273,146 A | * | 9/1966 | Hurwitz, Jr. ............ | B61L 25/04 310/322 |
| 6,260,415 B1 | * | 7/2001 | Goebel .................... | G01D 5/48 73/582 |
| 7,053,524 B2 | * | 5/2006 | Edmonson ........... | G01N 29/022 310/313 D |
| 7,343,804 B2 | * | 3/2008 | Liu ..................... | B60C 23/0408 701/29.1 |
| 7,642,742 B2 | | 1/2010 | Curello et al. | |
| 7,652,488 B1 | * | 1/2010 | Lopatin .................... | F02K 9/08 324/637 |
| 7,926,356 B1 | * | 4/2011 | Lopatin ................ | G01N 33/222 73/767 |

(Continued)

FOREIGN PATENT DOCUMENTS

WO    2013063184    5/2013

OTHER PUBLICATIONS

International Search Report and written opinion issued in corresponding International Application No. PCT/US2013/065281 dated Apr. 2, 2014.

(Continued)

*Primary Examiner* — Laura Martin
*Assistant Examiner* — Rose M Miller
(74) *Attorney, Agent, or Firm* — Avery Dennison Retail Information Services, LLC

(57) ABSTRACT

This application generally relates to systems and methods of using Radio Frequency Identification (RFID) devices to remotely analyze objects and structures, and more particularly, this application relates to systems and methods of using RFID devices to remotely analyze properties and conditions of a surface of objects and structures.

9 Claims, 5 Drawing Sheets

(56) References Cited

U.S. PATENT DOCUMENTS

| | | | |
|---|---|---|---|
| 2004/0148117 A1* | 7/2004 | Kirshenbaum | G07C 1/00 |
| | | | 702/82 |
| 2006/0244606 A1 | 11/2006 | Li et al. | |
| 2006/0247967 A1* | 11/2006 | Prusik | G06Q 30/0241 |
| | | | 705/14.4 |
| 2007/0001862 A1* | 1/2007 | Zweig | G01K 1/024 |
| | | | 340/588 |
| 2008/0058652 A1 | 3/2008 | Payne | |
| 2009/0033480 A1 | 2/2009 | Tanemura | |
| 2009/0155918 A1 | 6/2009 | Payne et al. | |
| 2011/0160548 A1 | 6/2011 | Forster | |
| 2011/0241839 A1* | 10/2011 | Lal | G21H 1/02 |
| | | | 340/10.1 |
| 2011/0248732 A1 | 10/2011 | Zimmerman et al. | |
| 2012/0116683 A1 | 5/2012 | Potyrailo et al. | |

OTHER PUBLICATIONS

International Preliminary report on Patentability and Written Opinion issued in corresponding International Application No. PCT/US2013/065281 dated Apr. 21, 2015.

* cited by examiner

SYSTEM AND METHOD FOR RFID-BASED REMOTE MATERIAL ANALYSIS

CROSS-REFERENCE TO RELATED APPLICATION(S)

The present application claims priority from U.S. Provisional Application No. 61/714,357 filed Oct. 16, 2012, which is incorporated by herein by reference in its entirety.

TECHNICAL FIELD

The invention described in this application generally relates to systems and methods of using Radio Frequency Identification (RFID) devices to remotely analyze objects and structures, and more particularly, the invention described in this application relates to systems and methods of using RFID devices to remotely analyze properties and conditions of a surface of objects and structures.

BACKGROUND OF THE INVENTION

Measuring or detecting properties or conditions of objects or structures can provide useful information on the particular object or structure. For example, inspecting or testing an object or structure for properties or conditions such as stiffness, hardness, elasticity, and the like can provide useful guidance in determining the overall condition of the object or structure or whether the object or structure is suited for its intended use or for continuing use in a particular situation.

BRIEF SUMMARY OF THE INVENTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

An embodiment of a method of determining a physical quality of a material comprises receiving an acoustic waveform at a RFID-monitored resonator that is in communication with the material, wherein the acoustic waveform perturbs an oscillation in the RFID-monitored resonator, and wherein the material affects the oscillation in the RFID-monitored resonator in a manner that correlates to the physical quality of the material. The method further includes the steps of monitoring an electric characteristic of the oscillation in the RFID-monitored resonator, generating a signal that includes information about the electric characteristic, and transmitting a modulated RF signal that includes the information from the signal.

In another embodiment, an RFID-monitor resonator for determining a property of a material comprises a piezoelectric capacitor configured to be in physical communication with the material, an inductor in electrical communication with the piezoelectric capacitor to form an oscillator circuit, and an RFID chip in electrical communication with the oscillator circuit. The piezoelectric capacitor is configured to receive an acoustic waveform that perturbs an oscillation in the oscillator circuit, and wherein the oscillation is affected by the material in a manner that correlates to the physical quality of the material. Further, the RFID chip is configured to monitor an electrical property of the oscillator circuit and transmit a modulated RF signal with information relating to the electrical property.

Other features and advantages of the present invention will become apparent to those skilled in the art from the following detailed description. It is to be understood, however, that the detailed description of the various embodiments and specific examples, while indicating preferred and other embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

These, as well as other objects and advantages of this invention, will be more completely understood and appreciated by referring to the following more detailed description of the presently preferred exemplary embodiments of the invention in conjunction with the accompanying drawings, of which.

DETAILED DESCRIPTION OF THE INVENTION

The apparatus and methods disclosed in this document are described in detail by way of examples and with reference to FIGS. 1-5. Unless otherwise specified, like numbers in FIGS. 1-5 indicate references to the same, similar, or corresponding elements throughout the figures. It will be appreciated that modifications to disclosed and described examples, arrangements, configurations, components, elements, apparatuses, methods, materials, etc. can be made and may be desired for a specific application. In this disclosure, any identification of specific shapes, materials, techniques, arrangements, etc. are either related to a specific example presented or are merely a general description of such a shape, material, technique, arrangement, etc. Identifications of specific details or examples are not intended to be, and should not be, construed as mandatory or limiting unless specifically designated as such. Selected examples of apparatus and methods for providing RFID devices to facilitate determination of a material property or condition are hereinafter disclosed and described in detail with reference made to FIGS. 1-5.

Monitoring or measuring properties or conditions of an object or structure can provide information about the object or structure or the material that makes up the object or structure. In one example, measuring or monitoring the surface properties of an object can provide information about the state of the object. For example, measuring the hardness or softness of the surface of a fruit can provide information about the ripeness of the fruit. In another example, measuring the stiffness, hardness, or elasticity of the surface of a wounded area of a human body can provide information about the state of the wound. For example, if blood has clotted on the surface of the wound to form a scab that covers the wound, the surface of the wound may be harder than if the wound remained open. In one example, a method of monitoring or measuring the properties or conditions of an object includes directing acoustic energy to the surface of the object and evaluating the acoustic energy reflected by the surface of the object to calculate or otherwise determine a property or condition of the object or the material comprising the object. Other applications are also possible and contemplated by this disclosure, including, but not limited to, food-monitoring applications, medical applications, mechanical or material applications, structural situations, fluid applications, and gas monitoring applications.

In one example, a radio frequency identification (RFID) device can be coupled to a resonator or oscillator circuit. The resonator or oscillator circuit can be placed in contact with a surface of an object or structure to facilitate a measurement or monitoring of the stiffness, hardness, elasticity, or other such properties or conditions of the surface of the object or structure or the material that is used to construct or make up the object or structure.

Figure 1:
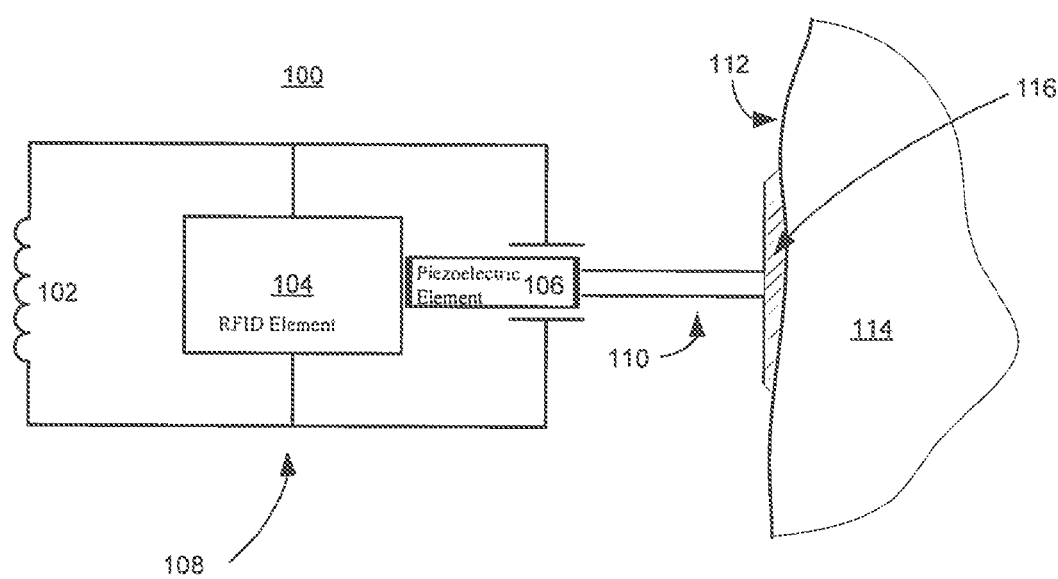
FIG. 1 is a schematic illustration depicting a RFID-monitored resonator circuit for analyzing the properties or conditions of an object or structure.

Referring now to FIG. 1, a schematic illustration of an RFID-monitored resonator 100 is shown. The RFID-monitored resonator 100 includes an inductor 102, an RFID element 104, and a piezoelectric capacitive element 106. Together, the inductor 102, RFID element 104, and piezoelectric capacitive element 106 comprise a resonator circuit 108. An intermediate connection structure 110 can couple the resonator circuit 108 to the surface 112 of an object or structure 114. Such an arrangement can facilitate the measuring or monitoring of a property or a condition of the structure 114 by the RFID-monitored resonator 100.

In one example, the intermediate connection structure 110 can be coupled to the surface 112 of the structure 114 to be monitored by an adhesive 116. It will be understood that the intermediate connection structure 110 can be coupled to the surface 112 of the structure 114 to be monitored by methods other than adhesives. For example, the intermediate connection structure 110 can be placed in contact with the surface 112 of the structure 114 to be monitored by a physical force or the intermediate connection structure 110 can be an integral component of the structure 114 to be monitored. It will be understood that by coupling the RFID-monitored resonator 100 to the structure 114, a number of methods can be used to measure or monitor properties or conditions of the structure 114.

The inductor 102 and piezoelectric capacitive element 106 can function as an oscillator circuit or resonator circuit. The RFID element 104 can be a RFID chip and can be use with an active RFID device, a passive RFID device, a battery assisted RFID device, or any other type of RFID device as would be understood by one familiar in the art. The RFID element 104 can be arranged to monitor the electric signal of the resonator circuit 108 and to output a radio frequency signal representative of the electric signal or any part of the electric signal of the resonator circuit 108. The RFID element 104 can also be arranged to analyze and/or modulate the electric signal of the resonator circuit 108 to include additional information before the RFID element 104 outputs a radio frequency signal representative of the electric signal. The RFID element 104 can be arranged to output a radio frequency signal representative of the electrical signal to an RFID reader (not shown), where the representative signal can further be analyzed or evaluated by hardware, firmware, or software. It will be understood that by outputting a radio frequency signal to a RFID reader or other such device, the RFID element 104 can facilitate the remote monitoring of a structure 114.

An electric signal passing through the resonator circuit 108 can be initiated, altered, or otherwise influenced by a flexing or bending motion of the piezoelectric capacitive element 106. By physically coupling the piezoelectric capacitive element 106 to the surface 112 of the structure 114, for example by using an intermediate connection structure 110, vibrations or other such disturbances at the surface 112 of the structure 114 can be relayed to the piezoelectric capacitive element 106 causing flexing, bending or other such motion of the piezoelectric capacitive element 106. Such flexing, bending or other such motion of the piezoelectric capacitive element 106 can in turn initiate, alter, or otherwise influence any electric signal of the resonator circuit 108.

In one example, an acoustic sound wave from an ultrasonic transducer can be used to generate vibrations at the surface 112 of the structure 114. The piezoelectric capacitive element 106 can detect such vibrations through the intermediate connection structure 110 and initiate or alter the electric signal of the resonator circuit 108. If the initial properties of the sound wave (e.g., wavelength, frequency, amplitude, etc.) are known, the physical effects of the sound wave on a surface 112 of a structure 114 can be determined as a function of stiffness, hardness, softness, elasticity, etc. of the surface 112. The physical effects of the sound wave on the surface 112 of the structure 114 can be detected by the piezoelectric capacitive element 106 through the intermediate connection structure 110 by the flexing or bending of the piezoelectric capacitive element 106. Such bending and flexing of the piezoelectric capacitive element 106 can affect the electric signal of the resonator circuit 108.

Evaluation of the change to the electric signal of the resonator circuit 108 due to the effect of the acoustic wave on the surface 112 of the structure 114 can be used to calculate or otherwise determine a property or condition, such as stiffness, hardness, softness, elasticity, etc., of the surface 112 of the structure 114. Such a calculation can be facilitated by knowing the initial properties of the sound wave and comparing those to the effect of the sound waves on the surface 112 of the structure 114. Such a calculation can be performed by the RFID element 104 or by an RFID reader (not shown). It will be understood that either the RFID element 104 or the RFID reader can be in communication with the ultrasonic transducer so that the initial properties of the sound waves are known, thus, facilitating a calculation of the properties or conditions of the surface 112 of the structure 114.

In another example, the motion of the piezoelectric capacitive element 106 can be initiated by applying an acoustic sound wave to the piezoelectric capacitive element 106. In such an arrangement the motion of the piezoelectric capacitive element 106 can be transferred to the surface 112 of the structure 114 through the intermediate connection structure 110. The surface 112 of the structure 114 can reflect the motion and alter (e.g., through dampening or magnifying) or otherwise affect the motion transferred by the piezoelectric capacitive element 106 as it is reflected back to the piezoelectric capacitive element 106. When that motion is reflected by the surface 112 of the structure 114 it is returned to the piezoelectric capacitive element 106 through the intermediate connection structure 110. The properties or conditions of the surface 112 can determine how the reflected motion is altered. Analysis of the electric signal of the resonator circuit 108 before and after the surface 112 has affected the motion of the piezoelectric capacitive element 106 can be used to calculate properties or conditions of the surface 112 of the structure 114.

Referring again to FIG. 1, a schematic representation of an intermediate connection structure 110 is shown for attaching the piezoelectric capacitive element 106 to the surface 112 of the structure 114 to be analyzed. As previously described, the intermediate connection structure 110 can be connected to the surface 112 of the structure 114 using an adhesive 116 such as glue, adhesive or other bonding material which would allow the connection structure to at least be temporarily bonded to the structure 114. The adhesive or bonding agent 116 can be selected so as to not substantially affect the resonance characteristics of the resonator circuit 108. The adhesive or bonding agent 116 can be selected so that the intermediate connection structure 110 can be removably attached to the surface 112, or merely to conduct the acoustic energy between the intermediate structure 110 and the surface 112 without actual adhering to the surface 112. The intermediate connection structure 110 can be rigid or pliable to conform to the surface 112, and can be selected so as to not substantially affect the resonance characteristics of the resonator circuit 108. For example, the intermediate connection structure 110 can be made of plastic, cellulosic materials or a polymer or other such materials. Alternatively the piezoelectric capacitive element 106 or the RFID-monitored resonator 100 can be directly attached or placed in contact with the surface 112 of the structure 114 to be monitored or measured. It will be understood that an adhesive, bonding agent or other such method can be used to facilitate attachment or contact between the piezoelectric capacitive element 106 or the RFID-monitored resonator 100 and the structure 114.

Figure 2:
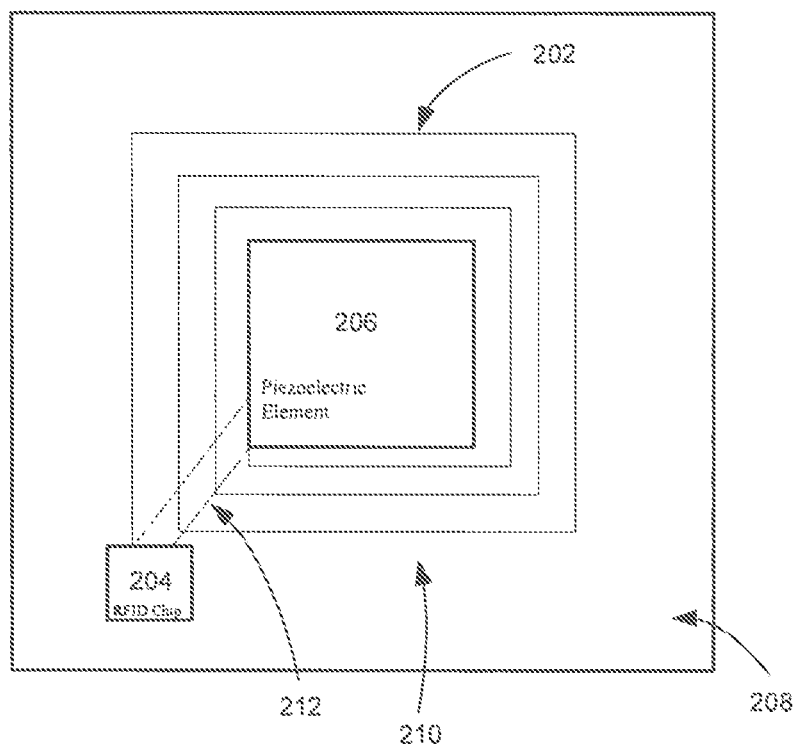
FIG. 2 is a schematic illustration depicting a RFID-monitored resonator in an embodiment of the disclosure.

Referring to FIG. 2, a schematic illustration of another embodiment of an RFID-monitored resonator 200 is shown. The RFID-monitored resonator 200 can include an inductor 202, a RFID chip 204, a piezoelectric capacitive element 206, an attachment label 208, and circuitry 212. The inductor 202, RFID chip 204, piezoelectric capacitive element 206, and circuitry 212 can collectively form a resonator circuit 210. The inductor 202 can be a conductive path or wire, for example a looped wire that is secured to the attachment label 208. The attachment label 208 can secure the RFID-monitored resonator 200 to a surface of an object or structure to be monitored. A separate connection means (not shown) such as for example the intermediate connection structure 110 and adhesive 116 shown in FIG. 1 and disclosed herein can separately connect the piezoelectric capacitive element 206 to the surface of an object or structure.

The RFID chip 204 can be an active RFID device, a passive RFID device, a battery assisted RFID device, or any other type of RFID device as would be understood by one familiar in the art. The RFID chip 204 can include a circuit, for example an integrated circuit, that monitors the electric signals of the resonator circuit 210. The RFID chip 204 can measure electric signals at points in the resonator circuit 210, for example through circuitry 212 connected to the inductor 202 and piezoelectric capacitive element 206, or by direct electrical connections to the inductor 202 and piezoelectric capacitive element 206. The piezoelectric capacitive element 206 can be a parallel plate capacitor that utilizes a piezoelectric material as the dielectric between the parallel plates of the capacitor. Example piezoelectric materials can include piezoelectric plastic such as polyvinylidene fluoride (PVDF) and other copolymers or piezoelectric ceramics such as lead zirconate titanate (PZT). Placing a voltage across the capacitor can cause mechanical changes in the piezoelectric material and can be used to create, among other things, an acoustic wave. Similarly, an acoustic wave or other mechanical perturbation applied to the piezoelectric capacitive element 206 can be used to alter the capacitance, create an electrical impulse, or both in the piezoelectric capacitive element 206. The changes in capacitance or electrical impulses can be used to perturb an oscillation in the resonator circuit 210. Other piezoelectric materials, different capacitor configurations, and other devices that have comparable or similar electrical properties could be used in place of, or in conjunction with, the piezoelectric capacitive element 206 as would be understood in the art.

The RFID chip 204 can receive an RF signal from an RF interrogator or RF reader, that turns on or wakes-up the RFID chip 204 when the chip receives sufficient energy of activation. The RFID chip 204 can be powered by the RF signal, by a battery, capacitor or by other means. The RFID chip 204 can trigger an oscillation in the resonator circuit 210, for example by applying a waveform or electrical impulse to the resonator circuit 210. The oscillation in the resonator circuit 210 can also be triggered by the acoustic wave.

The RFID chip 204 can monitor the electrical signals in the resonator circuit 210 and then send a radio frequency or RF-modulated signal to other devices for analysis. For example, the radio frequency or RF-modulated signal sent by the RFID chip 204 can be representative of information derived from the electrical signals, in addition to identifying information programmed into the RFID chip 204. For example, the RFID chip 204 can send an RF-modulated signal that includes information representative of the RMS or root mean squared power of the electrical signal present in the resonator circuit 210. An RFID chip 204 can also send more complicated analyses of the electrical signal, for example if the RFID chip 204 performs digital signal processing as would be commonly understood in the art. An RFID chip 204 can be configured with an initial calibration that can be used when taking a measurement to scale the measure or provide an offset to the measurement. An RFID chip 204 can also be configured to report factors that can affect the measurement such as temperature and humidity, or perform adjustments to the measurement taking temperature and other factors into account. In various configurations, the RFID chip 204 can include an internal antenna, the RFID chip 204 can use the inductor 202 as an antenna, or the RFID chip 204 can be connected to an antenna such as another wire loop (not shown) attached to the attachment label 208. In a configuration, the inductor 202 can be configured in a pattern that facilitates its use as both an inductor 202 and an antenna.

In one embodiment, power can be obtained parasitically by collecting and storing energy present in the resonator circuit 210. For example, an acoustic sound wave from an ultrasonic transducer can be directed at the RFID-monitored resonator 200 for a period of time (for example approximately several tens to hundreds of milliseconds) to generate an oscillation in the resonator circuit 210. Power in the resonator circuit 210 due to the oscillation can be collected by the RFID-monitored resonator 200 and stored for later use. For example, power can be stored and then used to trigger an oscillation in the resonator circuit 210. Power can also be stored in a battery (not shown), or capacitor (not shown), and collected using a photovoltaic or solar cell (not shown). Other power sources could also be used as would be understood in the art.

Figure 3:
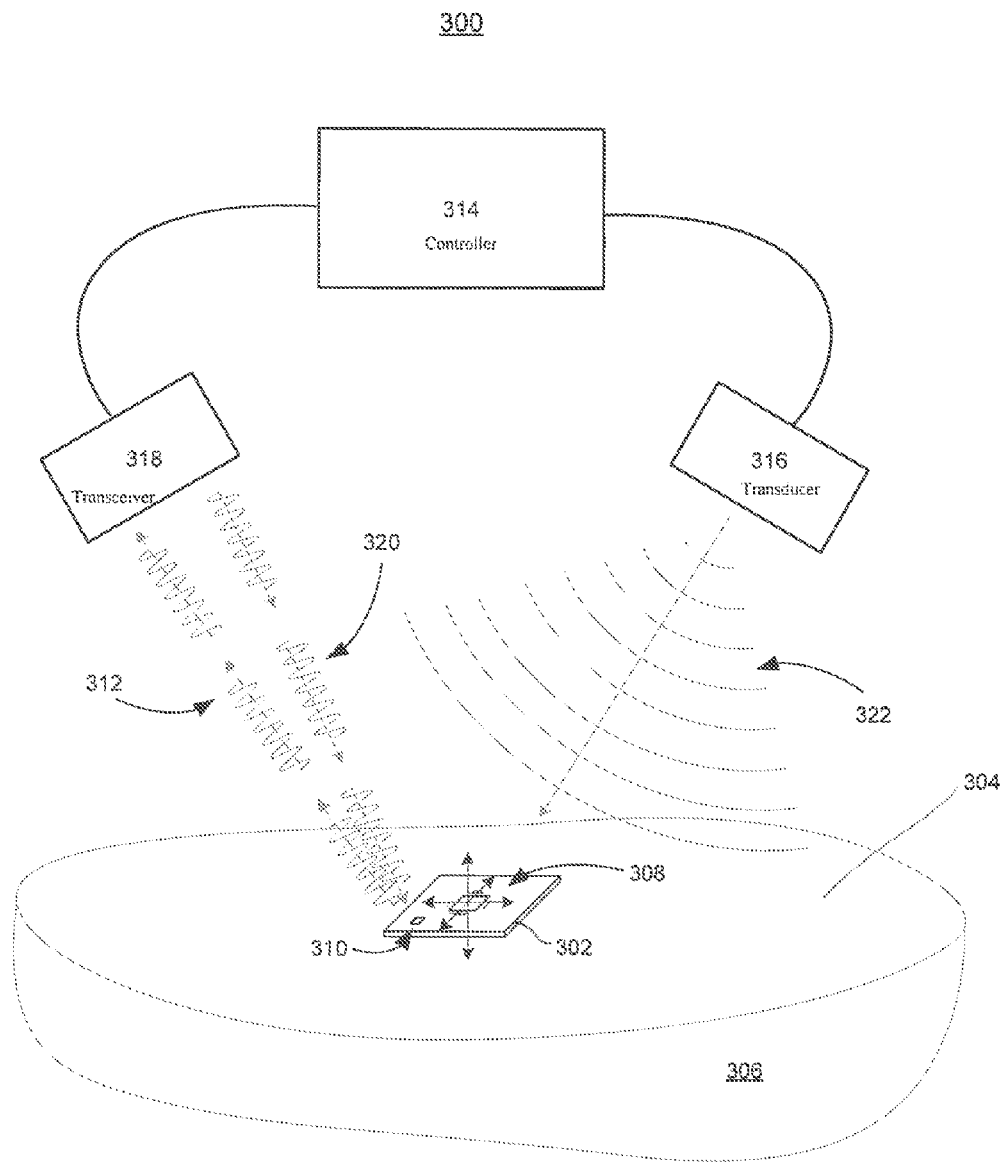
FIG. 3 is a schematic illustration depicting a system for transmitting acoustic energy to a RFID-monitored resonator mounted on the surface of an object or structure to be analyzed in an embodiment of the disclosure.

FIG. 3. is a schematic illustration of a system 300 that transmits acoustic energy to an RFID-monitored resonator 302 mounted on the surface 304 of an object or structure 306 to be analyzed. In response to the transmission of acoustic energy, the RFID-monitored resonator 302 sends a radio frequency (RF) transmission that includes information related to a physical property of the structure 306. The RFID-monitored resonator 302 can include a piezoelectric capacitive element 308 that is part of an oscillator circuit (not shown) and a RFID chip 310. The RFID chip 310 in the RFID-monitored resonator 302 can send information about electrical characteristics of the oscillations in the RFID-monitored resonator 302 by modulating a modulated RF signal 312 with information. Similar to previous descriptions, the modulated RF signal 312 can be representative of information derived from electrical signals of the RFID-monitored resonator 302, in addition to including information programmed into the RFID chip 310.

The system 300 can include a controller 314 that coordinates the actions of an ultrasonic transducer 316 and receives information from the RF transceiver 318. The RF transceiver 318 can be an RF interrogator or RF reader as would be familiar to one skilled in the art. The controller 314 can trigger the RF transceiver 318 to send an interrogating RF signal 320 to the RFID-monitored resonator 302 that wakes-up the RFID chip 310. The interrogating RF signal 320 can power the RFID chip 310 and, in some embodiments, provide power for triggering an initial oscillation in the oscillator circuit as described above. The controller 314 triggers the ultrasonic transducer 316 to send an acoustic sound wave 322 towards the surface 304 of the structure 306 and the RFID-monitored resonator 302. For example an ultrasonic acoustic wave 322 at a frequency of approximately 30 to 40 KHz for approximately several tens to hundreds of milliseconds can be directed towards the surface 304 and RFID-monitored resonator 302. Energy from the acoustic sound wave 322 can vibrate and/or cause mechanical perturbations in the piezoelectric capacitive element 308. The vibrations and/or mechanical perturbations can cause the piezoelectric capacitive element 308 to change capacitance, generate an electric signal, or a combination of both. This is turn alters the frequency of the oscillator circuit in the RFID-monitored resonator 302, or the amplitude or frequency response of the oscillation, present in the oscillator circuit, or both.

The RFID chip 310 can monitor properties of the oscillation or signal such as, for example, frequency and/or amplitude that are present in the oscillator circuit. The RFID chip 310 can produce and transmit a modulated RF signal 312 that is modulated with information regarding the signal present in the oscillator circuit. In various configurations, the RFID chip 310, or a signal processing device, can further analyze the signal, for example by performing digital signal processing on the signal as is known in the art before transmitting the modulated RF signal 312 to the RF transceiver 318. The RF transceiver 318 can receive the modulated RF signal 312 from the RFID-monitored resonator 302 and demodulate the modulated RF signal 312 to recover the information. The information can be sent to the controller 314 for further analysis, digital signal processing of the information, and/or presentation of information to a user. The user can be located remotely form the structure 306 being monitored and analyzed.

Figure 4A:
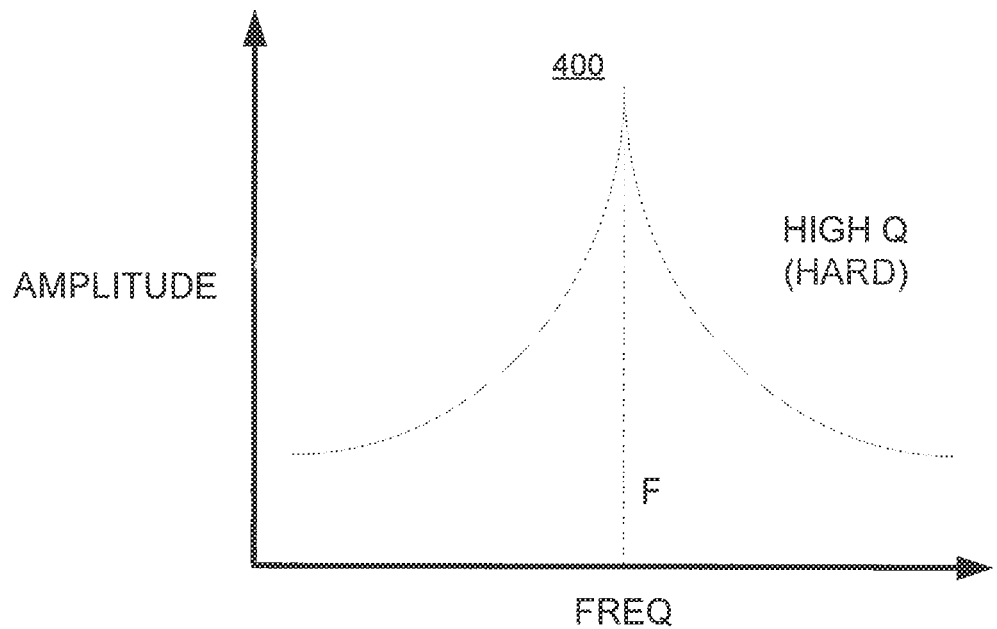
FIG. 4A is a graph diagram illustrating the frequency response curve of a RFID-monitored resonator attached to a hard material in an embodiment of the disclosure.
Figure 4B:
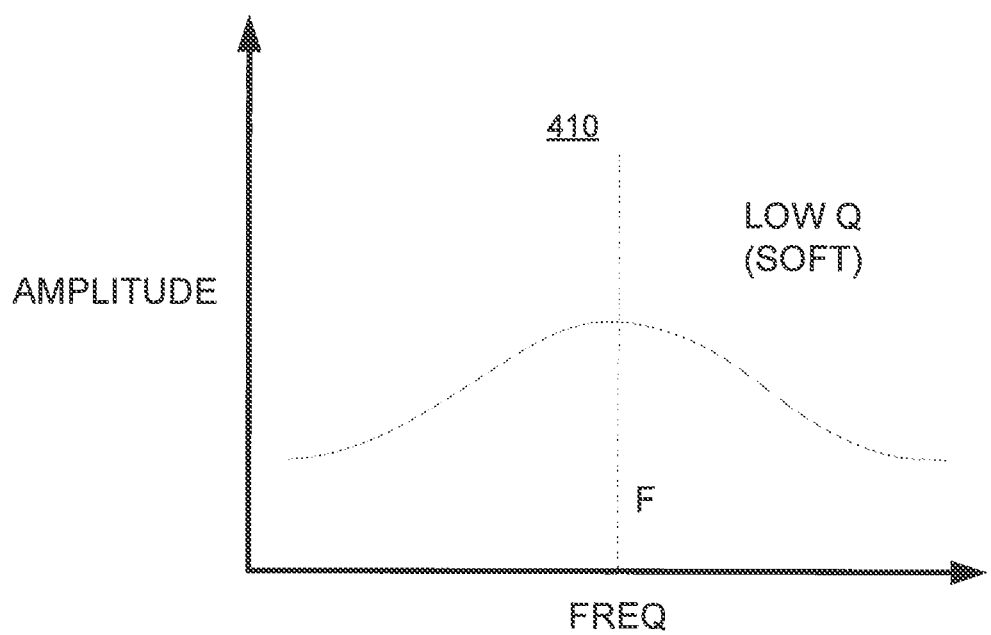
FIG. 4B is a graph diagram illustrating the frequency response curve of a RFID-monitored resonator attached to a soft material in an embodiment of the disclosure.

Referring now to FIGS. 4A and 4B, graph diagrams are presented that illustrate frequency response curves 400, 410 of examples of RFID-monitored resonators. In FIG. 4A, a frequency response curve 400 is present for an RFID-monitored resonator that is attached to a relatively hard material. The capacitive (C) and inductive (L) elements of FIGS. 1, 2 and 3 that make up the oscillator circuit have a characteristic resonant frequency (f) and quality factor (Q) that depend on the capacitive and inductive elements. In the configurations presented, the inductive element can remain substantially unchanged. However, the capacitive element can change due to the connection of a piezoelectric element to a surface of a structure being monitored. Since the capacitive element is connected to the surface of the structure, the impedance of the capacitive element in the oscillator circuit Q can change based upon the amount of energy lost through the connection. Thus, the Q of the oscillator circuit can be altered or otherwise changed. A hard surface can absorb less energy than a soft surface, and therefore, the Q of the oscillator circuit for a relatively hard surface at the resonant frequency (f) can be greater than the Q of the oscillator circuit for a relatively soft surface. In FIG. 4B, a frequency response curve 410 is presented for an RFID-monitored resonator that is attached to a relatively soft material. The frequency response curves 400, 410 illustrate that the Q, or quality factor, of the RFID-monitored resonator is greater for the resonator circuit when the piezoelectric element is attached to hard materials than when the piezoelectric element 106 is attached to soft materials. As will be understood, this difference in Q can be used to analyze the hardness or softness of the material under analysis.

Figure 5:
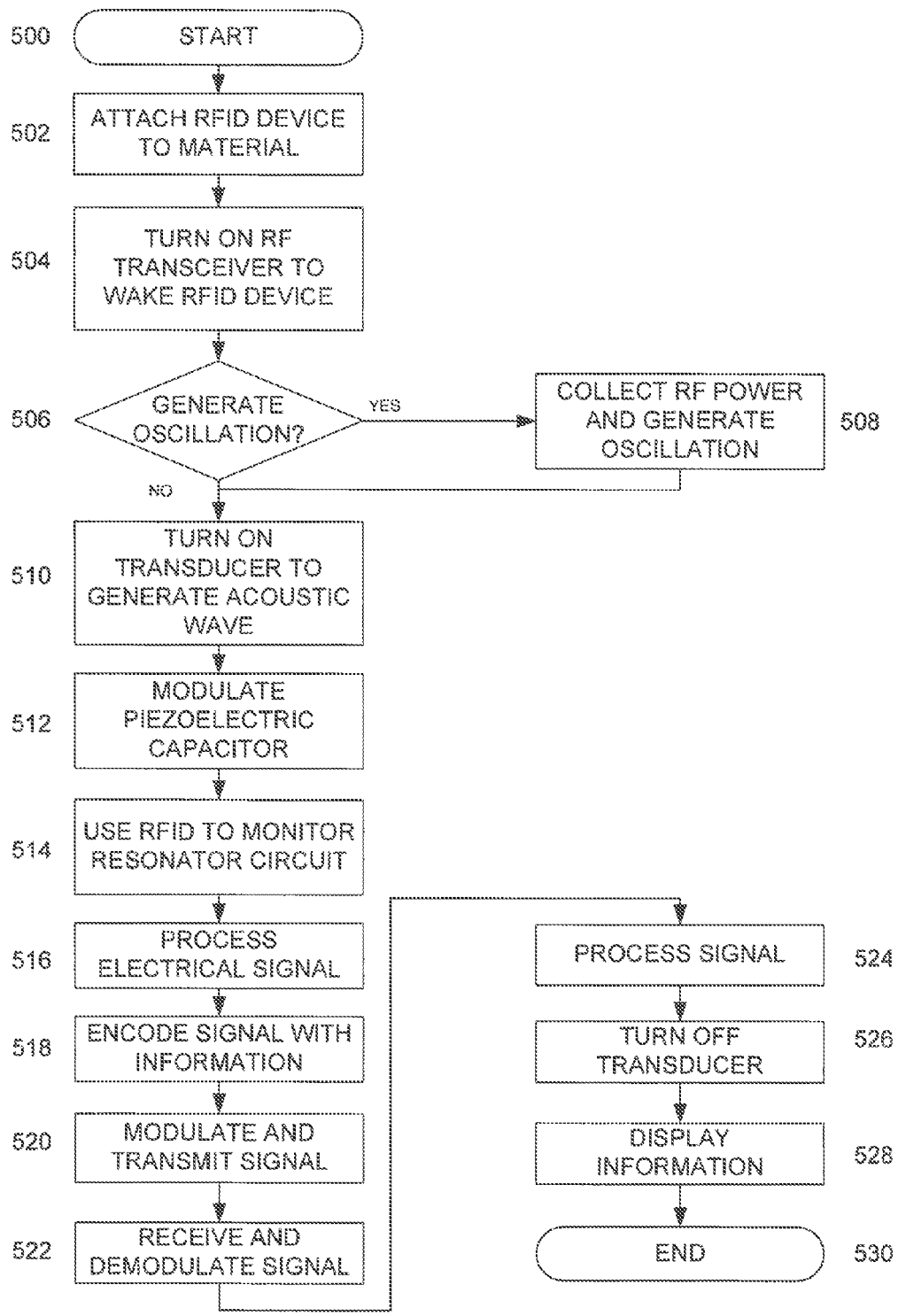
FIG. 5 is a flowchart diagram of a method for analyzing the properties or conditions of an object or structure using an RFID-monitored resonator in an embodiment of the disclosure.

Referring now to FIG. 5, a flowchart of one embodiment of an operation of a system for monitoring a physical property of a structure using an RFID-monitored resonator is presented. Operation starts with start block 500 labeled START. Processing continues to process block 502 where the RFID-monitored resonator is attached to a surface of a material to be analyzed. The RFID-monitored resonator can be attached using an attachment means such as a connection structure and/or an adhesive. Processing continues to process block 504.

In process block 504, a controller turns on a RF transceiver that sends an interrogation RF signal to a RFID chip. The RF transceiver can be an RF interrogator or RF reader as would be understood in the art. The interrogation RF signal from the RF transceiver wakes-up the RFID chip. Processing continues to decision block 506.

In decision block 506, if the RFID chip, or related circuitry is being used to generate the oscillation in the resonator or oscillator of the RFID-monitored then processing continues to process block 508 and then to process block 510, otherwise processing continues directly to process block 510. In process block 508, the RFID chip, or related circuitry, collects power from the interrogation RF signal and generates an initial oscillation in the resonator or oscillator circuit. Processing then continues to process block 510. In process block 510, the controller turns on an ultrasonic transducer to generate an acoustic sound wave that impinges on the RFID-monitored resonator mounted to the surface of the structure. Processing continues to process block 512.

In process block 512, the acoustic sound wave perturbs or modulates a piezoelectric capacitive element. The modulation generates or otherwise alters an oscillation in the resonator or oscillator circuit. Processing continues to process block 514.

In process block 514, the RFID chip of the RFID-monitored resonator samples or monitors the resonator or oscillator circuit to determine the electrical characteristics of the oscillation or signal present in the resonator or oscillator circuit as described herein. Processing then continues to process block 516. In process block 516, the RFID chip or other circuitry processes the electrical signal from the resonator or oscillator circuit. Processing continues to process block 518.

In process block 518, the RFID chip generates a signal by encoding within the signal information about the electrical signal in the resonator or oscillator circuit. The information can be a value indicative of the hardness of the surface of the structure under analysis. The RFID chip can encode additional information such as information about the temperature, an identification tag, and other such information. Processing continues to process block 520.

In process block 520, the RFID chip modulates an RF signal with the signal from process block 518 and transmits the RF signal. Processing continues to process block 522. In process block 522, the RF transceiver receives the modulated RF signal from the RFID chip and demodulates the RF signal to recover the information encoded in the signal. The RF transceiver transmits the signal, the information recovered from the signal, or both to the controller. Processing continues to process block 524.

In process block 524, the controller further processes the information in the signal. The controller process information from the RFID-monitored resonator to make a determination about the properties or conditions of the structure that the controller presents to the user in process block 528. Processing continues to process block 526. In process block 526, the controller turns off the ultrasonic transducer. Processing continues to process block 528. In process block 528, the controller presents the processed information to the user, for example, by displaying an indication of the hardness of the material, or in the case of fruit, the ripeness of the fruit. Processing terminates at end block 530 labeled END.

These and other configurations of RFID-monitored resonators and systems for monitoring a physical properties or conditions of objects, structures, or material using an RFID-monitored resonator can be used to monitor, analyze, and/or evaluate the physical properties and conditions of a surface of a structure and the material of the structure itself as would be recognized by those skilled in the art. The above descriptions of various components and methods are intended to illustrate specific examples and describe certain ways of making and using the systems disclosed and described here. These descriptions are neither intended to be nor should be taken as an exhaustive list of the possible ways in which these systems and modules can be made and used. A number of modifications, including substitutions of systems and modules between or among examples and variations among combinations can be made. Those modifications and variations should be apparent to those of ordinary skill in this area after having read this document. In addition, example methods may be better appreciated with reference to a flow diagram. While for purposes of simplicity of explanation, the illustrated methods are shown and described as a series of blocks, it is to be appreciated that the methods are not limited by the order of the blocks, as some blocks can occur in different orders and/or concurrently with other blocks from that shown and described. Moreover, less than all the illustrated blocks may be required to implement an example method. Blocks may be combined or separated into multiple components. Furthermore, additional and/or alternative methods can employ additional blocks that are not illustrated.

What is claimed is:

1. A method of determining a physical quality of a material, comprising:
   receiving an acoustic waveform at an RFID-monitored resonator, the RFID-monitored resonator includes an inductor and a piezoelectric capacitor that are in electrical communication and configured as an oscillator circuit and the RFID-monitored resonator is in communication with the material, wherein the acoustic waveform perturbs an oscillation in the RFID-monitored resonator, and wherein the material affects the oscillation in the RFID-monitored resonator in a manner that correlates to the physical quality of the material;
   coupling an intermediate structure to a surface of the material, so that the intermediate structure couples the oscillator circuit to the material;
   monitoring an electric characteristic of the oscillation in the RFID-monitored resonator;
   generating a signal that includes information about the electric characteristic; and
   transmitting a modulated RF signal that includes the information from the signal.

2. The method of claim 1, wherein the intermediate structure is secured to the surface of the material using an adhesive.

3. An RFID-monitor resonator for determining a property of a material, comprising:
   a piezoelectric capacitor configured to be coupled with the material by an intermediate structure on a surface of the material;
   an inductor in electrical communication with the piezoelectric capacitor to form an oscillator circuit; and
   an RFID element in electrical communication with the oscillator circuit;
   wherein the piezoelectric capacitor is configured to receive an acoustic waveform that perturbs an oscillation in the oscillator circuit; and
   wherein the oscillation is affected by the material in a manner that correlates to the physical quality of the material; and
   wherein the RFID element is configured to monitor an electrical property of the oscillator circuit and transmit a modulated RF signal with information relating to the electrical property.

4. A method for operation of a system for monitoring a physical property of a structure using an RFID-monitored resonator, comprising the steps of:
   providing a RFID monitored resonator which includes an inductor and a piezoelectric capacitor that are in electrical communication and configured as an oscillator circuit, the RFID monitored resonator has a RFID element;
   attaching the RFID-monitored resonator to a surface of a material to be analyzed;
   turning on an RF transceiver that sends an interrogation RF signal to the RFID element;
   collecting power from the interrogation RF signal to generate an initial oscillation in the RFID monitored resonator or oscillator;
   turning on an ultrasonic transducer to generate an acoustic sound wave that impinges on the RFID-monitored resonator mounted to the surface of the material, the acoustic sound wave perturbs or modulates a piezoelectric capacitive element, such that the modulation generates or otherwise alters an oscillation in the RFID monitored resonator or oscillator circuit;

sampling the resonator or oscillator circuit to determine an electrical characteristic of the oscillation or signal present in the resonator or oscillator circuit; and generating a signal by encoding within the signal information about an electrical signal in the RFID monitor resonator or oscillator circuit and wherein the signal information is a value indicative of a hardness of the surface of the material under analysis, such that RFID element can encode additional information.

5. The method of claim 4, including a further step of modulating the RF signal by the RFID element and the RF transceiver receives the modulated RF signal from the RFID chip and demodulates the RF signal to recover the information encoded in the signal after the step of generating the signal.

6. The method of claim 5, including a further step of transmitting the information recovered from the signal to a controller after the step of modulating.

7. The method of claim 6, including a further step of processing information from the RFID-monitored resonator to make a determination about properties or conditions of the material after the step of transmitting.

8. The method of claim 7, including a further step of presenting the processed information to a user by displaying an indication of a hardness of the material.

9. The method of claim 8, wherein the material is a fruit.

* * * * *